(12) United States Patent
Grawe et al.

(10) Patent No.: US 7,148,212 B2
(45) Date of Patent: *Dec. 12, 2006

(54) PROCESS FOR PRODUCTION OF STEROID CRYSTALS, STEROID CRYSTALS OBTAINED THEREBY AND PHARMACEUTICAL PREPARATIONS CONTAINING THEM

(75) Inventors: Detlef Grawe, Kleinromstedt (DE); Hagen Gerecke, Jena (DE); Peter Hoesel, Jena (DE); Annette Eichardt, Buergel (DE); Sabine Gliesing, Jena (DE); Uwe Mueller, Jena (DE)

(73) Assignee: Schering AG, Berlin (DE)

( * ) Notice: Subject to any disclaimer, the term of this patent is extended or adjusted under 35 U.S.C. 154(b) by 496 days.

This patent is subject to a terminal disclaimer.

(21) Appl. No.: 10/417,557

(22) Filed: Apr. 17, 2003

(65) Prior Publication Data
US 2003/0216360 A1    Nov. 20, 2003

(30) Foreign Application Priority Data
Apr. 23, 2002 (DE) ............................... 102 18 107

(51) Int. Cl.
*A61K 31/56* (2006.01)
*C07J 1/00* (2006.01)

(52) U.S. Cl. ...................... 514/179; 552/648
(58) Field of Classification Search ............... 552/648; 514/179
See application file for complete search history.

(56) References Cited

U.S. PATENT DOCUMENTS

| | | |
|---|---|---|
| 3,226,389 A | 12/1965 | Hertler |
| 5,266,712 A | 11/1993 | Lanquetin |
| 5,534,270 A * | 7/1996 | De Castro ............... 424/490 |
| 5,693,628 A * | 12/1997 | Schubert et al. ............ 514/179 |
| 5,871,771 A | 2/1999 | Zierenberg et al. |
| 2004/0006241 A1* | 1/2004 | Grawe et al. |

FOREIGN PATENT DOCUMENTS

| | | |
|---|---|---|
| EP | 0 522 700 A2 | 1/1993 |
| EP | 1157996 A1 * | 11/2001 |
| WO | 90/03782 | 4/1990 |
| WO | 92/08730 | 5/1992 |

OTHER PUBLICATIONS

Thilbert, R., et al: "Micronization of Pharmaceutical Solids" MML Series, vol. 1, Ch. 11, pp. 328-347.
Steckel, et al: "Micronizing of Steroids for Pulmonary Delivery . . . " International Journal of Pharmaceutics 152, 1997, pp. 99-110.
Susan Wendel et al: "An Overview of Spray-Drying Application", Pharmaceutical Technology, Oct. 1997, pp. 124-156.
B. Yu. Shekunov et al: "Crystallization Processes in . . . " Journal of Crystal Growth 211, 2000, pp. 122-136.
S. Halasz-Peterfi, et al: "Formation of Microparticles of Pharmaceuticals . . . " Industrial Crystallization 1999, pp. 1-11.
A. Affonso et al: "Microcrystallization Methods for Aspirin . . . " Journal of Pharmaceutical Sciences, vol. 60, No. 10, Oct. 1971, pp. 1572-1574.
Johnson, M.: "Particle Size Distribution of the Active Ingredient . . . " Pharmaceutica Acta Helvetiae, 1972, pp. 546-559.
Guitard, et al: "Maximale Zullaessige Partikel . . . " Pharm. Ind. 36, Nr. 1974, pp. 253-257, English Summary Only.

* cited by examiner

Primary Examiner—Barbara P. Badio
(74) Attorney, Agent, or Firm—Michael J. Striker

(57) ABSTRACT

The process for making steroid crystals having a predetermined average particle size of from 1 μm to 25 μm and a maximum particle size that does not exceed a predetermined maximum value of 100 μm, includes subjecting a supersaturated solution containing a steroid to a wet milling by wet milling apparatus while crystallizing, in order to obtain a primary particle suspension. Crystals obtained according to this process and pharmaceutical preparations containing them are also described.

17 Claims, 2 Drawing Sheets

PROCESS FOR PRODUCTION OF STEROID CRYSTALS, STEROID CRYSTALS OBTAINED THEREBY AND PHARMACEUTICAL PREPARATIONS CONTAINING THEM

BACKGROUND OF THE INVENTION

1. Field of the Invention

The invention relates to a process for production of steroid crystals, whose average particle size is in a predetermined range and whose maximum particle size does not exceed a predetermined value, to the steroid crystals obtained thereby and to the pharmaceutical preparations containing them, especially to low-dosage preparations.

2. Description of the Related Art

Most steroids are crystallized from a suitable solvent. A large-particle-sized crystallizate is produced in a conventional cooling or displacement crystallization. This crystallizate is micronized in a jet mill to obtain the required uniformity of effective-ingredient distribution (CUT) and dissolution kinetics, especially for low-dosage preparations. Average grain sizes of from 1.5 to 5 µm are obtained. An enormous increase in surface area as well as a thermodynamic activation of the surface occurs by partial amorphization and/or by considerable destruction or perturbation of lattice structure. A series of disadvantages are connected with this process, which are described in the literature (Thibert and Tawashhi: "Micronization of Pharmaceutical Solids", MML Series, Volume 1, Ch. 11, pp. 328–347). These disadvantages can be expressed strongly with different active ingredients. The effective ingredient can be strongly destablized by the partial amorphization. Chemical decomposition increases during interaction with the adjuvant substances in the pharmaceutical composition. An unstable physical structure is produced by recrystallization of the amorphous components. This leads to impairment of the dissolution properties and changes in the particle sizes during the precipitation of the effective ingredient, and also during preparation of the pharmaceutical composition. Agglomeration and incrustation occur during micronization, which leads to an undesirable particle size distribution in the micronizate. The particle size can be influenced only to a very limited degree during micronization. Lowering the milling pressure of course leads to a slight increase in the average particle size, but also to an undesirable increase in its spread. However a certain minimum pressure is absolutely required for operation of the mill.

Micronization as a process is only conditionally suited for manufacture of a physically and chemically stable steroid effective ingredient with a particle size adjusted to fit a certain dosage range. This is also true for alternative methods, such as manufacture of micro-fine effective ingredients from supercritical gases (Steckel, et al, "Micronizing of Steroids for Pulmonary Delivery by Supercritical Carbon Dioxide", Int. Journal of Pharmaceutics 152, pp. 99–110 (1997)). These methods are technologically demanding and very expensive because of the high pressures. Spray-drying (Wendel, et al, "An Overview of Spray-Drying Applications", Pharmaceutical Technology, October 1997, pp. 124–156) is similarly suitable for production of micro-fine particles, however there is a danger of producing unstable amorphous or partially crystalline structures.

It is known from the literature that fine grain size crystals can be produced by precipitation from highly supersaturated solutions or with high stirring speeds. (B. Yu. Shekunov, et al, "Crystallization Process in Pharmaceutical Technology and Drug Delivery Design", Journal of Crystal Growth 211, pp. 122–136 (2000); Halasz-Peterfi, et al, "Formation of Microparticles of Pharmaceuticals by Homogeneous Nucleation", Industrial Crystallization, 1999, pp. 1–11; Affonso, et al, "Microcrystallization Methods of Aspirin", Journal of Pharmaceutical Sciences, October 1971, pp. 1572–1574).

A suitable method for producing microcrystals by rapidly cooling and intensive mixing is described in U.S. Pat. No. 3,226,389. However these crystallizates often have a large scatter and particle size agglomerates are obtained. Also the desired production of a certain particle size distribution is only possible with difficulty because of the complex interplay of super-saturation, primary and second nuclei formation and crystal growth and/or agglomerate formation.

An additional possibility for producing a definite grain size spectrum of micro-fine steroid crystals, which depends on a mechanical procedure, is described in WO A 92/08730. A crystallizate is produced from a ternary mixture, which comprises a hydrophilic solvent, a lipophilic solvent and a surfactant, by cooling in this procedure. It is indeed finer than the starting material, however the low-dose preparation is still too coarse for many applications and the same disadvantages are present, which accompany crystallizates made from highly supersaturated solutions. Contamination of the effective ingredient with surfactant also occurs.

In EP 0 522 700 the possibility, which is part of the state of the crystallization arts, for providing seed crystals for crystal growth by further definite cooling and heating of a partial flow, which is fed back into the crystallization process is described. With this procedure a grain size increase is obtained in the first place to a grain size largely above 100 µm, in order to improve the filtration and growth processes to obtain a high purity.

The influence of particle size and form on the CUT-value for spherical particles in solid drugs is described in M. C. R. Johnson, "Particle Size Distribution of Active Ingredient for Solid Dosage Forms of Low Dosage", Pharmaceutica Acta Helvetiae, 47, pp. 546–559 (1972) and considering other forms in P. Guitard, et al, "Maximum Particle Size Distribution of Effective Ingredients for Solid Drugs in low dosage", Pharm. Ind. 36, Nr. 4 (1974). The maximum particle dimensions related to the respective dosages can be calculated from the relationships described therein.

The dissolution kinetics is another important parameter for evaluating or rating the usually only slightly water-soluble steroid microcrystals.

The pharmaceutical performance must be continuously tested by suitable standard tests. The same goes for stability of the microcrystals as active ingredients and in pharmaceutical preparations.

The isolation and drying procedures in all the described processes for producing microcrystals in suspensions for low dose preparations can be criticized. It is very difficult to dry fine-grained moist crystallizates, without impairing the grain size distribution.

SUMMARY OF THE INVENTION

It is an object of the present invention to provide a process for making steroid crystals, which does not have the disadvantages of the known prior art processes and which fulfills the requirements of low-dosage preparations.

According to the invention this object is attained by a process for making steroid crystals, whose average grain or particle size is in a predetermined range and whose maximum particle size does not exceeded a predetermined value. This process comprises subjecting a supersaturated solution containing the steroid to a wet milling by means of a wetting milling apparatus while crystallizing, in order to obtain a primary particle suspension.

The term "steroid", in the context of the present invention, means a naturally occurring or synthetic compound, which has the basic structural framework or sceleton of a (partially) hydrogenated cyclopenta[α]phenanthrene. For example, 11β-{4-[(ethylaminocarbonyl)oximinomethyl]phenyl}-17β-methoxy-17α-methoxymethyl-estra-4,9-dien-3-one (subsequently designated as J956), is a steroid, with which the present invention is illustrated.

With the process according to the present invention it is surprisingly possible to obtain steroid crystals which are sufficiently stable and which are adjusted in regard to their particle size parameter and thus correct in regard to pharmaceutical requirements for homogeneity of the active ingredient distribution (CUT) and dissolution kinetics for low-dosage formulations. Furthermore the grain size distribution for a certain dosage can be made with a high accuracy and reproducibility. Furthermore the process according to the invention can be performed simply, rapidly and in a cost-effective manner. The steroid crystals can preferably be isolated without impairing their grain size distribution and dried.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

Figure 1:
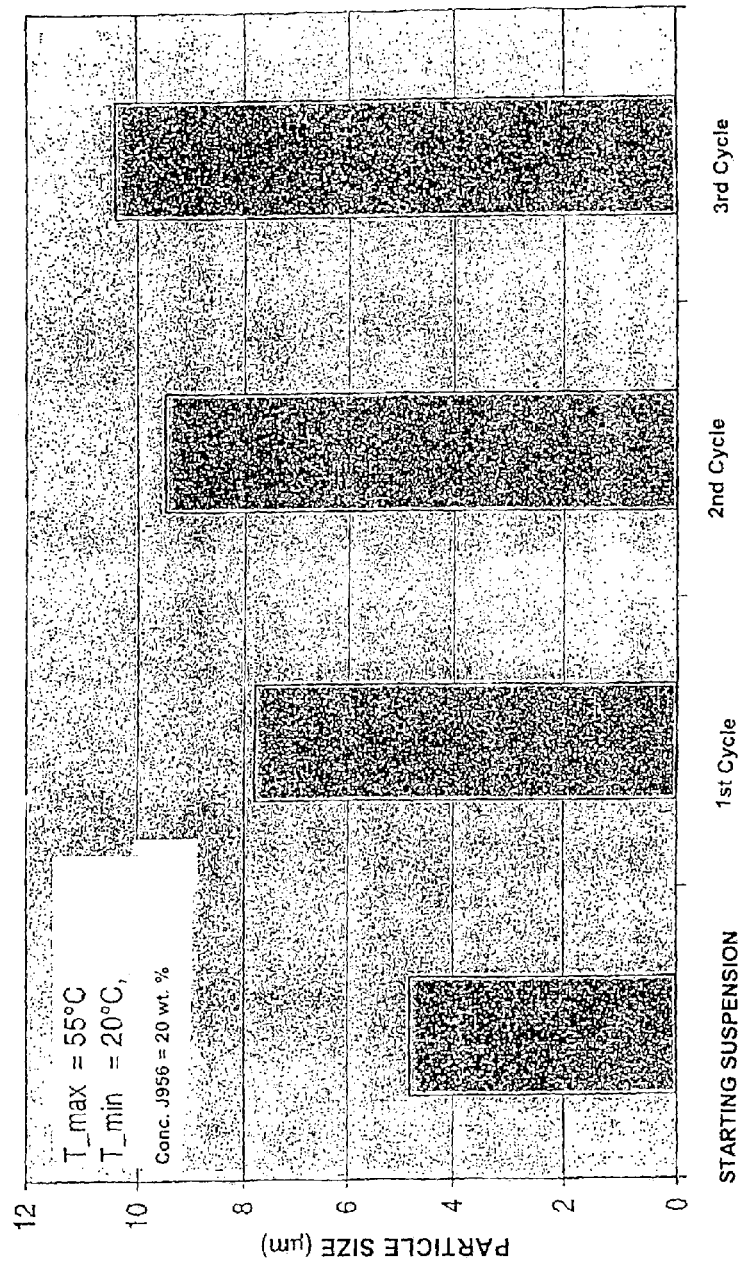
FIG. 1 is a graphical illustration of the behavior of the particle size in the crystallization process according to the invention.

The average particle size preferably amounts to from 1 μm to 25 μm, especially from 7 μm to 15 μm. The maximum particle size preferably does not exceed 100 μm, more preferably 80 μm. The "maximum particle size" means that no particle has a size that is greater than the stated value. Within these limits for the average particle size and the maximum particle size the particle size distribution is selected in a beneficial way so that the pharmaceutical specifications regarding CUT and dissolution kinetics correspond to those for low-dose formulations.

In the process according to the invention a supersaturated solution of the steroid is used. The solution contains the steroid as a solute, which is dissolved for that purpose in a solvent. The term "solvent" is understood to encompass mixtures of different solvents. A supersaturated solution used in the process according to the invention contains more dissolved material than it would when the solution is in thermodynamic equilibrium. Supersaturated solutions, in which crystal nuclei spontaneously form, can be used in the process according to the invention.

In a preferred embodiment of the process according to the invention the supersaturated solution contains from 1 percent by weight to 50 percent by weight, preferably 5 percent by weight to 35 percent by weight, of the steroid, in relation to the supersaturated solution. The above-described advantages of the process according to the invention can be achieved in an especially beneficial manner with these supersaturated solutions.

The preparations of the supersaturated solutions can occur in the usual manner. Preferably the supersaturated solution is made by dissolving the steroid in a solvent at a temperature below the boiling point and subsequently cooling to a temperature above the freezing point of the solution. If the steroid J956 is used for the steroid and ethyl acetate as the solvent for the supersaturated solution in the process according to the invention, the heating can occur, for example, at about 70° C., until the steroid has dissolved in the ethyl acetate and the resulting solution appears to be clear. Cooling can take place during a period from 10 minutes to one hour, preferably 15 minutes to 30 minutes, at about 35° C. One skilled in the art can ascertain the parameters for making a supersaturated solution with another solvent than ethyl acetate and with another steroid other than J956 by simple tests without more.

The crystallization is advantageously performed in a vessel, which is equipped with a stirrer. For example, the crystallization vessel can be equipped for that purpose.

In the process according to the invention wet milling is performed by a wet milling apparatus during crystallization. The crystallization can proceed from the saturated solution, since the wet milling has been started. Suitable apparatus for wet milling are dispersion tools and homogenizers, such as rotor-stator apparatuses, stirring mills, roller mills and colloid mills.

The manufacture of the crystals according to the invention occurs, as already described above, by crystallization from a solvent or solvent mixture, in which a wet milling by means of a wet milling apparatus, especially a rotor-stator apparatus or a colloid mill is performed. The wet milling is performed either shortly after crystallization has begun or before it has begun. The apparatus for wet milling can be used immediately as an additional stirring device in the crystallization vessel or in a by-pass loop that goes around the crystallization vessel. The use of the by-pass loop is especially beneficial, since the apparatus is used at the same time as a supply unit. If a rotor-stator apparatus is used, the peripheral rotation speed can be 10 m/s to 50 m/s, preferably 20 m/s to 40 m/s. A very high secondary nuclei formation rate is produced by the additional energy input caused by the wet milling, especially by the rotor-stator apparatus. The individual crystal growth is greatly reduced because of that energy input. Also the inevitably formed agglomerates are broken up in narrow gaps. Thus a fine primary particle size is the result, whose average particle size is between 3 μm and 25 μm and whose maximum particle size is not greater than 25 μm to 80 μm. These particle parameters can already be sufficient for low dose formulations.

In order to be able to make crystals that meet the pharmaceutical requirements, even for larger particle sizes, with a definite particle size distribution with suitable accuracy and better reproducibility, the primary suspension is preferably subjected to an oscillatory temperature profile. For that purpose the fine primary suspension produced is heated to a temperature $T_{max}$ below the solubility limit of the primary particles in the suspension and subsequently cooled slowly to a temperature $T_{min}$, which is above the freezing point of the suspension. On heating the fine-grained fraction of the primary particle suspension is dissolved and precipitated on the particle size fraction present during the cooling process. Because of that a definite shift in the particle size distribution to the larger range occurs. Preferably $T_{max}$ is selected so that between 10 and 95, preferably 20 to 50 and more preferably about 30, percent by weight of the primary particles are dissolved during the heating. The fraction of dissolved primary particles is selected according to the predetermined grain size, which again is determined by the type of low-dosage formulation. If a higher proportion of the primary particles dissolve, larger-sized particles result.

In a preferred embodiment of the process according to the invention $T_{min}$ is selected so that the dissolved primary particles substantially re-crystallize again. If it is particularly desirable to reduce the losses of steroid material, nearly all of the dissolved primary particles are re-crystallized on the still remaining primary particles.

It is especially preferable when the cooling from $T_{max}$ to $T_{min}$ occurs during 1 minute to 10 hours, especially during 0.5 hours to 2 hours.

The cooling side of the temperature profile should be controlled so that the fresh nuclei formation is kept as small as possible. The size of this coarsening depends on the amount of the crystallizates dissolved in the heating cycle, which again is determined by the position of both temperatures $T_{max}$ and $T_{min}$ in relation to the solubility limit and the solid concentration of the suspension. This heating-cooling cycle can be repeated often, preferably 1 to 20 times, until the desired particle size distribution is obtained. The controlling parameters are thus $T_{max}$, $T_{min}$ and the number of cycles. The more the desired coarsening, the less $T_{max}$ should be. Thus one can approach the desired final particle size with small steps. The development of the dissolved portion of the crystallizate in the heating periods is thus dimensioned so that the maximum particle diameter increases still only to a very small extent and the coarsening occurs in the region of the fine particles. Thus, for example, during dissolution and re-crstallization of 40 percent of the J956 precipitated from a 20 percent by weight ethyl acetate solution, the average particle diameter (×50) increases from 4.9 μm to 7.8 μm while the increase of the maximum particle size (×100) is scarcely measurable. That means that the particle size distribution is considerably narrowed during growth of the average value (×50) of the particle diameter. This effect is especially advantageous for pharmaceutical applications, especially for obtaining suitable CUT values and dissolution properties.

According to the invention a very fine and narrow particle size distribution can be obtained by suitable selection of the apparatus and process conditions, since the fine-grained fraction typical for milling methods is often reduced by the overlapping crystallization processes. The maximum particle size can be kept very small, since the agglomerate formation is largely avoided.

After passing through the oscillatory temperature profile the obtained crystal suspension can be filtered and washed with a solvent, since the steroid is only soluble to a small extent, for example less than 1 percent by weight. For example, these solvents are methyl-t.-butyl ether, hexane, heptane, water or mixtures of two or more of these solvents. Because of that in subsequent drying processes, which occur preferably by a drying gas or in vacuum directly in the filtration unit, bridge formation and agglomeration of the particles are avoided.

The drying can occur by convection or vacuum drying in a stirred or moving bed.

When a conventional filtration and drying is difficult and leads to impairment of the particle size distribution produced during the crystallization, for example in the case of very fine particle sizes, alternatively the filtered and washed filter cake is suspended with a suspending liquid. The suspending liquid should be a liquid, preferably water, in which the steroid is only slightly soluble, for example less than one percent by weight. The obtained suspension can be converted into the dried solid form of the steroid by spray drying.

The subject matter of the invention also includes steroid crystals, which are obtained by the above-described process according to the invention. To perform the process in the above-described manner, the detailed description of the process here is referred to.

The subject matter of the invention also includes pharmaceutical formulations or preparations, which contain the steroid crystals obtained according to the process of the invention.

An example of a suitable capsule recipe or formula is provided in Table I.

TABLE I

SUITABLE CAPSULE RECIPE FOR COMPOSITION CONTAINING 1 MG OF J956

| SUBSTANCE | AMOUNT |
|---|---|
| J956, microcrystalline | 1.000 mg |
| Microcrystalline cellulose | 102.480 mg |
| Magnesium stearate | 0.520 mg |
| Hard gelatin capsule, size 3 | 1 piece |
| Capsule filling mass | 104.000 mg |

In Table II an example of a suitable tablet recipe is provided.

TABLE II

SUITABLE TABLET RECIPE FOR COMPOSITION CONTAINING 1 MG OF J956

| CORE: | |
|---|---|
| J956, microcrystalline | 1.00 mg |
| Lactose monohydrate | 33.8 mg |
| Corn starch | 18.0 mg |
| Maltodextrin (10% water) | 6.0 mg |
| Na carboxymethyl starch | 0.6 mg |
| Glycerol monobehenate | 0.6 mg |
| SHELL: | |
| Hydroxypropylmethyl cellulose | 1.125 mg |
| Talcum | 0.225 mg |
| Titanium dioxide | 0.625 mg |
| Iron oxide, yellow pigment | 0.020 mg |
| Iron oxide, red pigment | 0.005 mg |

An essential result of the invention is that steroid microcrystals are obtained, which are chemically considerably more stable than currently known micronizates, since first they have a reduced specific surface area and second they have crystalline surfaces that are unperturbed and highly crystalline.

Another result is that the steroid microcrystals obtained by the process according to the invention correspond in regarding to their particle size distribution and solubility properties to the pharmaceutical requirements of drugs regarding CUT and dissolution properties.

It has been shown that the obtained release values and grain size distribution uniformity (CUT) of the microcrystals of the invention are not inferior to those using micronized solids of the prior art for comparison (Table IV to Table VII) for the 1 mg capsule and 1 mg tablet examples. The release values were compared in a test medium, which comprises 0.3% SDS in water, with paddle stirring, 100 rpm.

TABLE III

J956: COMPARATIVE RELEASE VALUES IN % FOR COMPARISON OF 1 mg CAPSULE WITH A MICRONIZED EFFECTIVE INGREDIENT TO 1 mg CAPSULE WITH MICROCRYSTALLINE SOLIDS

| PARTICLE DIAMETER (μm) | | RELEASE in % | | | | |
|---|---|---|---|---|---|---|
| X50 | X100 | 0 min | 10 min | 20 min | 30 min | 45 min |
| 3.4 | 25 | 0 | 90.7 | 97.3 | 98.1 | 99.9 |
| 5.2 | 30 | 0 | 89.8 | 93.5 | 93.4 | 95.6 |
| 6.6 | 43 | 0 | 93.2 | 95.9 | 96.7 | 96.8 |
| 8.7 | 43 | 0 | 93.5 | 96.7 | 98.5 | 99.7 |
| 14.1 | 87 | 0 | 90.2 | 95.3 | 96.0 | 96.3 |
| Micronizate | | 0 | 92.1 | 94.3 | 94.6 | 94.9 |

TABLE IV

J956: CUT VALUE SPREAD FOR 1 mg CAPSULE WITH A MICRONIZED EFFECTIVE INGREDIENT VERSUS 1 mg CAPSULE WITH MICROCRYSTALLINE SOLIDS PARTICLE DIAMETER (μm)

| X50 | X100 | Confidence Interval % | RSD, % |
|---|---|---|---|
| 3.4 | 25 | 2.23 | 3.56 |
| 5.2 | 30 | 1.20 | 2.08 |
| 6.6 | 43 | 1.08 | 1.57 |
| 8.7 | 43 | 0.93 | 1.38 |
| 14.1 | 87 | 1.77 | 2.50 |
| Micronizate | | 1.72 | 2.56 |

TABLE V

J956: COMPARATIVE RELEASE VALUES IN % FOR COMPARISON OF 1 mg TABLET WITH A MICRONIZED EFFECTIVE INGREDIENT TO 1 mg TABLET WITH MICROCRYSTALLINE SOLIDS
Test Medium: 0.3 % SDS in water, paddle, 100 rpm

| PARTICLE DIAMETER (μm) | | RELEASE in % | | | | |
|---|---|---|---|---|---|---|
| X50 | X100 | 0 min | 10 min | 20 min | 30 min | 45 min |
| 10.6 | 73 | 0 | 73.7 | 90.3 | 91.85 | 96.6 |
| Micronizate | | 0 | 92.1 | 94.3 | 94.6 | 94.9 |

TABLE VI

J956: CUT VALUE SPREAD FOR 1 mg TABLET WITH A MICRONIZED EFFECTIVE INGREDIENT VERSUS 1 mg TABLET WITH MICROCRYSTALLINE SOLIDS PARTICLE DIAMETER (μm)

| X50 | X100 | Confidence Interval % | RSD, % |
|---|---|---|---|
| 10.6 | 73 | 1.16 | 1.70 |
| Micronizate | | 1.72 | 2.56 |

Figure 2:
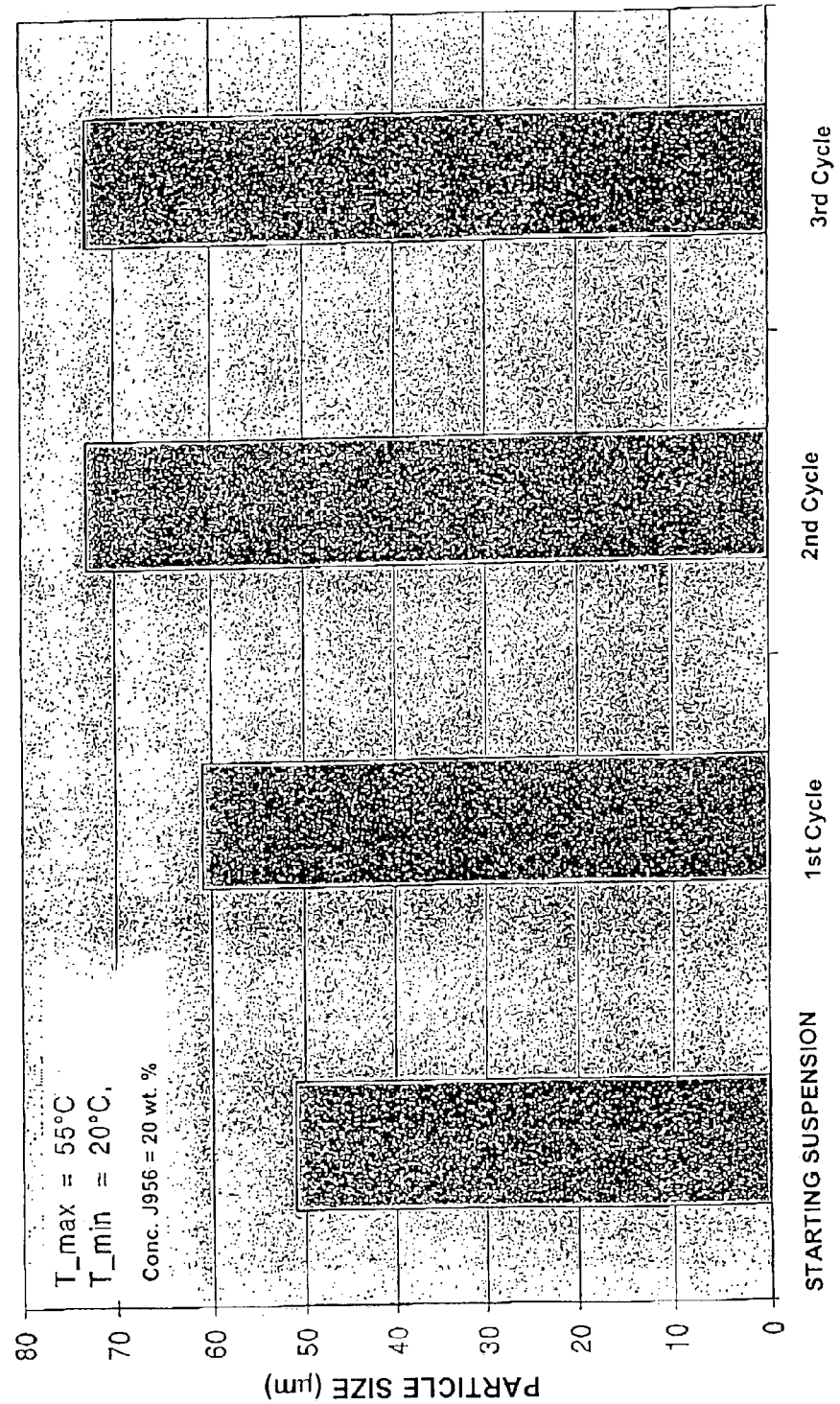
FIG. 2 is another graphical illustration of the behavior of the particle size in the crystallization process according to the invention

A further important result is that the pharmaceutically required particle size distribution of the steroids can be produced with higher reproducibility and accuracy with the process according to the invention. In FIGS. 1 and 2 the development of the grain size or particle size in the crystallization process is illustrated. The scatter of the particle size distribution is clearly reduced and the maximum grain size is clearly only slightly increased in spite a multiple increase in the average particle size. This assists in attaining good CUT values, also for low-dosage formulations.

Furthermore the grain size distribution produced in the suspension also is maintained in the dried solid body.

TABLE VII

PARTICLE SIZE DISTRIBUTION BEFORE AND AFTER DRYING

| | X10 | X50 | X90 | X100 |
|---|---|---|---|---|
| Suspension* | 2.62*** | 10.4 | 24 | 73 |
| After drying on filter | 2.7 | 10.61 | 24 | 73 |
| Suspension** | 2.11 | 8.6 | 19 | 51 |
| After spray-drying | 2.25 | 8.03 | 17 | 43 |

*suspension of J956 in ethyl acetate with 14% by weight microcrystalline J956
**suspension of J956 in ethanol/water (90/10) with 10% by weight microcrystalline J956
***particle diameters in μm The following measurement procedures were used to obtain measured experimental data.

Particle Size Distribution:
Sympatec HELOS (H0445), dry dispersion system (RO-DOS), pressure 2 bar Content Uniformity Test:
Content Determination according to USP/Ph. Eur. for individual capsules after elution through HPLC with external calibration
Column: LiChrosphere 5μ RP-18 encapped, 150×3 mm
Eluent: acetonitrile/water=45/55
Flow: 1 ml/min
Detection UV (272 nm)

Active Ingredient Release:
Active ingredient release measured in 1000 mL water with 0.3% sodium dodecyl sulfate, 100 rpm
Content Determination y HPLC with external calibration
Column: LiChrosphere 5μ RP-18 encapped, 150×3 mm
Eluent: acetonitrile/water=45/55
Flow: 1 ml/min
Detection UV (272 nm)

The following examples serve to illustrate the invention, but do not limit the broad concept of the invention expressed generally above or in the claims appended below.

EXAMPLES

Example 1

In a glass reactor with an anchor agitator and a double-wall heating/cooling jacket 250 g of J956 are dissolved in 1100 ml ethyl acetate at 70° C. The clear solution is cooled for 30 minutes at 35° C. A rotor-stator dispersing apparatus (Ultra Turrax, T25 basic, with S25N-25F) is used to prepare this solution. It is operated with a rotation speed of 12000 to 18000 rpm. After 2 to 5 minutes crystallization begins. The Ultra Turrax is operated for an additional 10 minutes and then is shut off.

The starting suspension obtained is heated at 55° C. and subsequently cooled within an interval of 1 hour 20 minutes to 20° C. This procedure is repeated still twice more.

Subsequently the filter cake is dried with air.

Microcrystals are obtained with the following particle size distribution:

| Particle size (μm) | |
| --- | --- |
| X10 | 2.62 |
| X50 | 10.4 |
| X100 | 73 |

Example 2

In a sulfonation flask with a blade mixer and a heating/cooling bath 50 g of J956 are dissolved in 200 g of ethyl acetate at 70° C. The clear solution is cooled for 15 minutes at 35° C. A rotor-stator dispersing apparatus (Ultra Turrax, T25 basic, with S25N-25F) is operated with a rotation speed of 12000 to 18000 rpm to prepare the solution. After 2 minutes crystallization begins. The Ultra Turrax is operated for an additional 10 minutes and then is shut off.

The starting suspension obtained is heated at 50° C. and subsequently cooled within an interval of 1 hour at 20° C. This procedure is repeated still twice more.

Subsequently the suspension is filtered by means of a frit and washed with 100 ml MTBE. The filter cake is washed with 1000 ml water very thoroughly and subsequently suspended with 300 g water. The suspension is spray-dried under the following conditions in a laboratory spray-drier with two nozzles (2 mm) (QVF/Yamato):

| | |
| --- | --- |
| Drying gas entrance temperature: | 170° C. |
| Drying gas exit temperature: | 60° C. |
| Drying gas throughput: | 23 m³/min |
| Spray nozzle (d = 2 mm) | 2.5 bar |
| Feed: | 8 to 10 ml/min |

Microcrystals are obtained in a separating filter of the spray-drier with the following particle size distribution:

| Particle size (μm) | |
| --- | --- |
| X10 | 1.75 |
| X50 | 6.04 |
| X100 | 36 |

Example 3

In a glass reactor with an anchor agitator and a double-wall heating/cooling jacket 270 g of J956 are dissolved in 1200 ml of ethyl acetate at 75° C. The clear solution is cooled for 30 minutes at 38° C. The solution is circulated from the crystallizing vessel bottom outlet and is then fed back into the crystallizing vessel by means of an external rotor-stator dispersing apparatus (IKA laboratory Pilot 2000/4 with DR module). The rotor-stator dispersing apparatus is operated with a rotation speed of 9000 rpm. After 2 to 5 minutes crystallization begins. The rotor-stator dispersing apparatus is operated for an additional 10 minutes and then is shut off.

The primary particle suspension obtained is heated at 50° C. and subsequently cooled within an interval of 1 hour 20 minutes to 20° C. This procedure is repeated still twice more. Subsequently the filter cake is filtered by a frit and washed with 500 ml MTBE. The filter cake is dried by suction with air.

Microcrystals are obtained with the following particle size distribution:

| | PARTICLE SIZE (μm) | |
| --- | --- | --- |
| | Primary particle size | Final |
| X10 | 3 | 4 |
| X50 | 9 | 13 |
| X100 | 61 | 73 |

Example 4

In a glass reactor with an anchor agitator and a double-wall heating/cooling jacket 270 g of J956 are dissolved in 1200 ml of ethyl acetate at 75° C. The clear solution is cooled for 30 minutes at 26° C. The solution is circulated from the crystallizing vessel bottom outlet and is then fed back into the crystallizing vessel by means of an external rotor-stator dispersing apparatus (IKA laboratory Pilot 2000/4 with DR module). The rotor-stator dispersing apparatus is operated with a rotation speed of 8900 rpm. After 30 sec at 36° C. crystallization begins. The rotor-stator dispersing apparatus is operated for an additional 10 minutes and then is shut off.

The primary particle suspension obtained is heated at 55° C. and subsequently cooled within an interval of 2 hours at 20° C. This procedure is repeated still twice more. Subsequently the filter cake is filtered with a frit and washed with 500 ml MTBE. The filter cake is dried by suction with air.

Microcrystals are obtained with the following particle size distribution:

| | PARTICLE SIZE (μm) | |
| --- | --- | --- |
| | Primary particle size | Final |
| X10 | 1.2 | 1.4 |
| X50 | 3.4 | 5.4 |
| X100 | 30 | 30 |

Example 5

In a glass vessel 63 g of testosterone undecanoate are dissolved in 130 ml of acetone and cooled to 18° C. A rotor-stator dispersing apparatus (Ultra Turrax, T25 basic, with S25N-25F) is used to prepare this solution. It is operated with a rotation speed of 12000 to 16000 rpm. After 1 minute crystallization begins. The Ultra Turrax is operated for an additional 10 minutes and then is shut off. The primary particle suspension obtained is subsequently heated at 21° C. and subsequently cooled within an interval of 30 minutes at 5° C. The suspension is filtered and washed with hexane.

The filter cake is dried by suction with air.

Microcrystals are obtained with the following particle size distribution:

| PARTICLE SIZE (μm) | | |
|---|---|---|
| | Primary particle size (μm) | 1st Cycle (μm) |
| X10 | 6 | 17 |
| X50 | 21 | 41 |
| X99 | 100 | 100 |
| X100 | 120 | 120 |

Example 6

In a glass vessel 13 g of gestagen are dissolved in 130 ml of ethyl acetate (2.3% vol) mixture and cooled to 35° C. A rotor-stator dispersing apparatus (Ultra Turrax, T25 basic, with S25N-25F) is used to prepare this solution. It is operated with a rotation speed of 22000 rpm. After 1 minute crystallization begins. The Ultra Turrax is operated for an additional 10 minutes and then is shut off. The primary particle suspension obtained is subsequently heated at 45° C. and subsequently cooled within an interval of 30 minutes at 15° C. The suspension is filtered and washed with hexane.

The filter cake is dried by suction with air.

Microcrystals are obtained with the following particle size distribution:

| PARTICLE SIZE (μm) | | |
|---|---|---|
| | Primary particle size (μm) | End (μm) |
| X10 | 4 | 8 |
| X50 | 15 | 21 |
| X99 | 51 | 51 |
| X100 | 61 | 61 |

Example 7

In a glass vessel 28 g of norethisterone acetate are dissolved in 140 ml of methanol and cooled to 29° C. A rotor-stator dispersing apparatus (Ultra Turrax, T25 basic, with S25N-25F) is used to prepare this solution. It is operated with a rotation speed of 22000 rpm. After 1 minute crystallization begins. The Ultra Turrax is operated for an additional 10 minutes and then is shut off. The primary particle suspension obtained is subsequently heated at 34° C. and subsequently cooled within an interval of 1 hour 15 minutes at 5° C. The suspension is filtered and washed with hexane.

The filter cake is dried by suction with air.

Microcrystals are obtained with the following particle size distribution:

| PARTICLE SIZE (μm) | | |
|---|---|---|
| | Primary particle size (μm) | End (μm) |
| X10 | 4 | 8.5 |
| X50 | 14 | 30.4 |
| X99 | 55 | 87 |
| X100 | 87 | 100 |

Example 8

In a glass vessel 50 g of methylnortestosterone are dissolved in 250 ml of ethanol and cooled to 20° C. A rotor-stator dispersing apparatus (Ultra Turrax, T25 basic, with S25N-25F) is used to prepare this solution. It is operated with a rotation speed of 22000 rpm. At the same time 375 ml of water are added. Crystallization begins immediately. The Ultra Turrax is operated for an additional 10 minutes and then is shut off. The primary particle suspension obtained is subsequently cooled at 21° C. The suspension is filtered and washed with water, suspended in water to form a 10% suspension and spray-dried.

Microcrystals are obtained with the following particle size distribution:

| PARTICLE SIZE (μm) | | |
|---|---|---|
| | Primary particle size (μm) | Spray-dried (μm) |
| X10 | 1.32 | 1.36 |
| X50 | 3.96 | 3.94 |
| X99 | 14 | 14 |
| X100 | 18 | 18 |

Example 9

Manufacture of Hard Gelain Capsules with Microcrystalline J-956

| SUBSTANCE | AMOUNT |
|---|---|
| Carbamate J-956, microcrystalline | 1.000 mg |
| Microcrystalline cellulose | 102.480 mg |
| Magnesium stearate | 0.520 mg |
| Hard gelatin capsule, size 3 | 1 piece |
| Capsule filling mass | 105.000 mg |

The microcrystalline J-956 is mixed in a suitable mixer (e.g. container mixer) with the microcrystalline cellulose. The magnesium stearate is added and mixed several times. The absence of water is tested in a testing unit. The mixture is filled with a suitable capsule filling machine (e.g. Harro Hoeflinger, KFMIIIC) in hard gelatin capsules, size 3.

Example 10

Manufacture of Soft Gelatin Capsules with Testosterone Undecanoate

| | |
|---|---|
| Capsule Filling Material: | |
| Testosterone undecanoate, microcrystalline | 40.000 mg |
| Oleic Acid | 210.000 mg |
| Capsule Jacket: | |
| Propylene glycol | 22.53 mg |
| Glycerol, 85% | 28.66 mg |
| Gelatin | 101.37 mg |
| Titanium dioxide | 1.42 mg |
| Iron oxide yellow | 0.11 mg |

The testosterone undecanoate is dissolved in the oleic acid. The solution is filled in soft capsules grade 5, oval.

Example 11

Manufacture of Tablets with Norethisterone Acetate

| | | |
|---|---|---|
| Norethisterone acetate, microcrystalline | Ph.Eur. | 1.000 mg |
| Lactose monohydrate | Ph.Eur. | 82.000 mg |
| Potato starch | Ph.Eur. | 36.450 mg |
| Additives: | | |
| Gelatin | Ph.Eur. | 1.350 mg |
| Talcum | Ph.Eur. | 5.400 mg |
| Magnesium stearate | Ph.Eur. | 0.700 mg |
| Carboxymethyl starch sodium (type A) | Ph.Eur. | 2.700 mg |
| Pure water as 4% drying loss | | 5.400 mg |

The microcrystalline norethisterone acetate is granulated with lactose and potato starch in a fluidized bed granulator with an aqueous gelatin solution. The granulate is mixed with magnesium stearate and talcum and a mass of 135 mg is pressed on a rotary press to form a tablet.

The disclosure in German Patent Application 102 18 107.1 of Apr. 23, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a process for production of steroid crystals, steroid crystals obtained thereby and pharmaceutical preparations containing them, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A process for making steroid crystals, said steroid crystals having an average particle size of from 1 µm to 25 µm and a maximum particle size of 100 µm, said process comprising subjecting a supersaturated solution containing a steroid to a wet milling by a wet milling apparatus while crystallizing, in order to obtain a primary particle suspension.

2. The process as defined in claim 1, wherein said supersaturated solution contains from 1 to 50 percent by weight of said steroid, based on said supersaturated solution.

3. The process as defined in claim 1, further comprising preparing said supersaturated solution by dissolving said steroid in a solvent at a temperature below a boiling point of said solvent to form a resulting solution and subsequently cooling said resulting solution to a temperature above a freezing point of the resulting solution.

4. The process as defined in claim 1, wherein said crystallizing is performed in a vessel or container having a stirring device.

5. The process as defined in claim 1, wherein said wet milling apparatus is a rotor-stator apparatus, a stirring mill, a roller mill or a colloid mill.

6. The process as defined in claim 1, further comprising heating said primary particle suspension to a temperature ($T_{max}$) below a solubility limit of primary particles of the primary particle suspension and subsequently cooling to a temperature above a freezing point ($T_{min}$) of the primary particle suspension.

7. The process as defined in claim 6, wherein said supersaturated solution comprises a solvent and said temperature ($T_{max}$) below said solubility limit is selected so that from 10 to 95 percent by weight of said primary particles dissolve in said solvent.

8. The process as defined in claim 7, wherein said temperature above said freezing point ($T_{min}$) is selected so that dissolved primary particles are substantially re-crystallized.

9. The process as defined in claim 8, wherein said cooling from said temperature ($T_{max}$) below said solubility limit to said temperature above said freezinf point ($T_{min}$) occurs during a time interval of 1 minute to 10 hours.

10. The process as defined in claim 6, wherein said heating to said temperature ($T_{max}$) below said solubility limit and said cooling to said temperature above said freezing point is performed from 1 to 20 times.

11. Steroid crystals having an average particle size of from 1 µm to 25 µm and a maximum particle size of 100 µm, wherein said steroid crystals are made by a process comprising subjecting a supersaturated solution containing a steroid to a wet milling by a wet milling apparatus while crystallizing, in order to obtain a primary particle suspension.

12. The steroid crystals as defined in claim 11, wherein said supersaturated solution contains from 1 to 50 percent by weight of said steroid, based on said supersaturated solution, and said process comprises preparing said supersaturated solution by dissolving said steroid in a solvent at a temperature below a boiling point of said solvent to form a resulting solution and subsequently cooling said resulting solution to a temperature above a freezing point of the resulting solution.

13. The steroid crystals as defined in claim 11, wherein said supersaturated solution comprises a solvent; said process comprises heating said primary particle suspension to a temperature ($T_{max}$) below a solubility limit of primary particles of the primary particle suspension and subsequently cooling to a temperature above a freezing point ($T_{min}$) of the primary particle suspension and wherein said temperature ($T_{max}$) below said solubility limit is selected so that from 10 to 95 percent by weight of said primary particles dissolve in said solvent and said temperature above said freezing point ($T_{min}$) is selected so that dissolved primary particles are substantially re-crystallized, said cooling from said temperature ($T_{max}$) below said solubility limit to said temperature above said freezing point ($T_{min}$) occurs during a time interval of 1 minute to 10 hours.

14. The steroid crystals as defined in claim 11, wherein said crystallizing is performed in a vessel or container having a stirring device and said wet milling apparatus is a rotor-stator apparatus, a stirring mill, a roller mill or a colloid mill.

15. A pharmaceutical preparation containing steroid crystals, said steroid crystals having an average particle size of from 1 µm to 25 µm and a maximum particle size of 100 µm, wherein said steroid crystals are made by a process comprising subjecting a supersaturated solution containing a steroid to a wet milling by a wet milling apparatus while crystallizing, in order to obtain a primary particle suspension.

16. The pharmaceutical preparation as defined in claim 15, wherein said crystallizing is performed in a vessel or container having a stirring device and said wet milling apparatus is a rotor-stator apparatus, a stirring mill, a roller mill or a colloid mill.

17. The pharmaceutical preparation as defined in claim 15, wherein said supersaturated solution contains from 1 to 50 percent by weight of said steroid, based on said supersaturated solution, and said process comprises preparing said supersaturated solution by dissolving said steroid in a solvent at a temperature below a boiling point of said solvent to form a resulting solution and subsequently cooling said resulting solution to a temperature above a freezing point of the resulting solution.

* * * * *